United States Patent
Garcia et al.

(10) Patent No.: US 10,028,911 B2
(45) Date of Patent: Jul. 24, 2018

(54) SUSTAINED RELEASE FORMULATION OF METHOTREXATE AS A DISEASE-MODIFYING ANTIRHEUMATIC DRUG (DMARD) AND AN ANTI-CANCER AGENT

(71) Applicant: PACIRA PHARMACEUTICALS, INC., San Diego, CA (US)

(72) Inventors: Louie Daniel Garcia, San Diego, CA (US); Lois Gibson, Bradley Beach, CA (US); William Joseph Lambert, North Potomac, MD (US); Benjamin W. Li, San Diego, CA (US); Liangjin Zhu, San Diego, CA (US)

(73) Assignee: Pacira Pharmaceuticals, Inc., San Diego, CA (US)

( * ) Notice: Subject to any disclaimer, the term of this patent is extended or adjusted under 35 U.S.C. 154(b) by 23 days.

(21) Appl. No.: 13/786,323

(22) Filed: Mar. 5, 2013

(65) Prior Publication Data

US 2013/0183370 A1    Jul. 18, 2013

Related U.S. Application Data

(62) Division of application No. 12/914,944, filed on Oct. 28, 2010.

(Continued)

(51) Int. Cl.
*A61K 9/127* (2006.01)
*A61K 9/00* (2006.01)

(Continued)

(52) U.S. Cl.
CPC ............ *A61K 9/127* (2013.01); *A61K 9/0019* (2013.01); *A61K 31/198* (2013.01); *A61K 31/25* (2013.01);

(Continued)

(58) Field of Classification Search
CPC ...................................................... A61K 9/127

(Continued)

(56) References Cited

U.S. PATENT DOCUMENTS 4,565,696 A * 1/1986 Heath et al. ............... 424/193.1
5,422,120 A   6/1995 Kim (Continued)

FOREIGN PATENT DOCUMENTS

GB    2443738        5/2008
WO    99/25319    *  5/1999

(Continued)

OTHER PUBLICATIONS

Bonetti, et al., An extended-release formulation of methotrexate for subcutaneous administration, Cancer Chemotherapy and Pharmacology, vol. 33, pp. 303-306, 1994.

(Continued)

*Primary Examiner* — Gollamudi Kishore
(74) *Attorney, Agent, or Firm* — Knobbe Martens Olson & Bear LLP

(57) ABSTRACT

Disclosed is are formulations comprising a multivesicular liposome and MTX, the administration of which results in a $C_{max}$ of MTX between 5% and 50% of the $C_{max}$ of an immediate release dosage form of MTX, the duration of which lasts from about 1 to about 30 days. Also disclosed are methods of treating autoimmune diseases and cancer by administering these formulations of MTX.

24 Claims, 3 Drawing Sheets

Related U.S. Application Data

(60) Provisional application No. 61/334,546, filed on May 13, 2010.

(51) Int. Cl.
   *A61K 31/198*   (2006.01)
   *A61K 31/25*    (2006.01)
   *A61K 31/519*   (2006.01)
   *A61K 31/575*   (2006.01)
   *A61K 31/685*   (2006.01)

(52) U.S. Cl.
   CPC .......... *A61K 31/519* (2013.01); *A61K 31/575* (2013.01); *A61K 31/685* (2013.01)

(58) Field of Classification Search
   USPC ........................................................ 424/450
   See application file for complete search history.

(56) References Cited

U.S. PATENT DOCUMENTS

| | | | |
|---|---|---|---|
| 5,723,147 A * | 3/1998 | Kim et al. | 424/450 |
| 5,759,573 A * | 6/1998 | Kim | 424/450 |
| 5,766,627 A | 6/1998 | Sankaram et al. | |
| 5,891,467 A | 4/1999 | Willis et al. | |
| 6,132,766 A | 10/2000 | Sankaram et al. | |
| 6,171,613 B1 | 1/2001 | Ye et al. | |
| 6,306,432 B1 * | 10/2001 | Shirley et al. | 424/450 |
| 2003/0162234 A1 * | 8/2003 | Jallad et al. | 435/7.23 |
| 2006/0116334 A1 * | 6/2006 | Hendrix | 514/27 |
| 2007/0009434 A1 * | 1/2007 | Low et al. | 424/1.49 |
| 2007/0065541 A1 * | 3/2007 | Keller et al. | 426/72 |
| 2007/0093497 A1 * | 4/2007 | Walsh | 514/251 |
| 2007/0235889 A1 | 10/2007 | Hartouian et al. | |
| 2009/0110735 A1 | 4/2009 | Maggio | |
| 2009/0232731 A1 * | 9/2009 | Funk et al. | 424/1.21 |

FOREIGN PATENT DOCUMENTS

| | | |
|---|---|---|
| WO | WO 1999/25319 | 5/1999 |
| WO | WO 2006/029385 | 3/2006 |
| WO | WO 2006/122414 | 11/2006 |
| WO | WO 2008/009476 | 1/2008 |
| WO | WO 2008/030818 | 3/2008 |

OTHER PUBLICATIONS

Chatelut et al., A slow-release methotrexate formulation for intrathecal chemotherapy, Cancer Chemotherapy and Pharmacology, vol. 32, pp. 179-182, 1993.

Chatelut et al., Sustained-Release Methotrexate for Intracavitary Chemotherapy, Journal of Pharmaceutical Sciences, vol. 83, No. 3, Mar. 1993.

Chladek et al., Low-Dose Methotrexate Pharmacokinetics and Pharmacodynamics in the Therapy of Severe Psoriasis; Basic & Clinical Pharmacology & Toxicology; vol. 96, Issue 3, pp. 247-248, Published Online Feb. 25, 2005; Mar. 2005.

Felson et al., American College of Pheumatology Preliminary Definition of Improvement in Rheumatiod Arthritis; Arthritis & Rheumatism, vol. 38, No. 6, Jun. 1995.

Hiraga et al., Pharmacokinetics and efficacy of low-dose methotrexate in patients with rheumatoid arthritis; Modern Rheumatology; vol. 14, No. 2, pp. 135-142; 2004.

Hoekstra et al., Factors associated with toxicity, final dose, and efficacy of methotrexate in patients with rheumatiod arthritis; Ann Rheum Dis, 62:423-426; 2003.

Hoekstra et al., Bioavailability of higher dose methotrexate comparing oral and subcutaneous administration in patients with rheumatoid arthritis; Journal of Rheumatology; vol. 31 No. 4; pp. 645-648; Apr. 1, 2004.

Hornung et al., Patients with Rheumatoid Arthritis Treated with Methotrexate (MTX): Concentrations of Steady-state Erythrocyte MTX Correlate to Plasma Concentrations and Clinical Efficacy; The Journal of Rheumatology; vol. 35 No. 9; pp. 1709-1715; Sep. 1, 2008.

Kim et al., Preparation of Multivesicular Liposomes, Biochimica et Biophysica Acta, vol. 728, pp. 339-348, 1983.

Link et al., The Effect of Adjuvant Chemotherapy on Relapse-Free Survival in Patients with Osteosarcoma of the Extremity; New England Journal of Medicine; 314 (No. 25): 1600-1606; Jun. 19, 1986.

McKendry et al., Adverse effects of low dose methotrexate therapy in rheumatoid arthritis; Journal of Rheumatology; vol. 20; pp. 1850-1856; Nov. 1993.

Ortiz et al., The efficacy of folic acid and folinic acid in reducing methotrexate gastrointestinal toxicity in rheumatoid arthritis—A metaanalysis of randomized controlled trials; J. Rheumatol, 25 (1998) 36-43.

Prey et al. Effect of folic or folinic acid supplementation on methotrexate-associated safety and efficacy in inflammatory disease: a systematic review; Br J Dermatol. 2009;160:622-628.

Shoda et al., Higher Maximal Serum Concentration of Methotrexate Predicts the Incidence of Adverse Reactions in Japanese Rheumatoid Arthritis Patients; Modern Rheumatology; vol. 17, No. 4, pp. 311-316, 2007.

Stamp et al., The use of low dose methotrexate in rheumatoid arthritis—are we entering a new era of therapeutic drug monitoring and pharmacogenomics?, Biomedicine & Pharmacotherapy, vol. 60, pp. 678-687, 2006.

Sweierkot, J. and J. Szechinski, 2006. Methotrexate in rheumatoid arthritis. Pharmacol. Rep., 58: 473-492.

International Search Report and Written Opinion dated Jul. 27, 2001 for PCT/US2011/036328.

International Preliminary Report on Patentability (Chapter II), dated Apr. 16, 2012 for PCT Application No. PCT/US2011/036328, filed May 12, 2011.

Chinese Office Action dated Oct. 8, 2013 in Application No. 201180023882.8.

Chinese Office Action dated Aug. 11, 2014 in Application No. 201180023882.8.

Extended European Search Report dated May 20, 2014 in Application No. 11781306.3.

\* cited by examiner

SUSTAINED RELEASE FORMULATION OF METHOTREXATE AS A DISEASE-MODIFYING ANTIRHEUMATIC DRUG (DMARD) AND AN ANTI-CANCER AGENT

INCORPORATION BY REFERENCE TO RELATED APPLICATIONS

Any and all priority claims identified in the Application Data Sheet, or any correction thereto, are hereby incorporated by reference under 37 CFR 1.57. The present application is a divisional application, and claims the benefit of priority to U.S. patent application Ser. No. 12/914,944, entitled "SUSTAINED RELEASE FORMULATION OF METHOTREXATE AS A DISEASE-MODIFYING ANTI-REHEUMATIC DRUG (DMARD) AND AN ANTI-CANCER AGENT," filed Oct. 28, 2010, which claims the benefit of priority to U.S. Provisional Patent Application Ser. No. 61/334,546, filed May 13, 2010, each of which is hereby incorporated by reference in its entirety.

BACKGROUND OF THE INVENTION

Field of the Invention

The present application relates to multivesicular liposome (MVL) formulations of methotrexate (MTX) which minimize the side effects of MTX while maintaining or improving efficacy.

Background Information

MTX is the primary first-line disease-modifying antirheumatic drug (DMARD) for rheumatoid arthritis (RA) and has demonstrated efficacy in other autoimmune diseases. MTX has also been used to treat certain cancers and cancer conditions. Cancer is a leading cause of death in the United States. Despite significant efforts to find new approaches for treating cancer, the primary treatment options remain surgery, chemotherapy and radiation therapy, either alone or in combination.

Over 500,000 patients are treated with immediate release MTX formulations worldwide (Sweierkot and Szechinski, *Pharmacol Reports*, 58, 473-492 (2006)). Because MTX causes significant plasma concentration-related side effects after each dose (nausea, vomiting, abdominal discomfort, taste disturbance, anorexia, dyspepsia, and diarrhea), it is usually taken once per week, on Saturday, so that the patient recovers by the work week. Side effects are primarily induced by high $C_{max}$, which is a pharmacokinetic term meaning the maximum plasma concentration of the drug. At common efficacious doses, up to 80% of patients suffer these side effects and up to 35% of patients ultimately discontinue use of MTX even though it offers excellent efficacy in most patients (see R. J. McKendry et al., *J Rheumatol* 20:1850 (1993)). While many of the side effects of MTX appear to be gastrointestinal, some of them (for example nausea and vomiting) may be central nervous system (CNS) side effects so subcutaneous rather then oral administration does not necessarily ameliorate side effects.

Recent recommendations for the use of MTX in RA suggest that oral administration of MTX should be started at 10-15 mg/wk with escalation up to 20-30 mg/wk. High dose oral administration (>15 mg) is known to result in lower bioavailability than subcutaneous administration. This is due to the active absorption of MTX in the small intestine, a process which is capable of being saturated at higher doses (Stamp et al., *Biomed Pharmacother* 60 678-687 (2006)). Thus, parenteral administration can be used in cases of inadequate clinical response or intolerance for oral administration.

For RA, the efficacy of MTX is not related to the maximum plasma concentration ($C_{max}$) of MTX but is directly related with its plasma area under the curve ("AUC") (Hiraga et al., *Mod Rheumatol* 14:135 (2004)). MTX AUC correlates well with intracellular levels of MTX-polyglutamate, the latter of which are thought to provide the anti-inflammatory effect (Hornung et al., *J. Rheumatol*, 35, 1709-1715 (2008)). The standard AUC for oral immediate release dosage forms of MTX is 2466 mcg/L-hr. (Hoekstra et al., *J Rheumatol*, 31 645-48 (2004). The standard AUC for subcutaneous immediate release dosage forms of MTX is 3786 mgc/L-hr. Id.

Because orally administered MTX is absorbed rapidly ($t_{max}$ 1-3 hour) and cleared rapidly ($t_{1/2}$ 8-10 hours), $C_{max}$ is difficult to control with conventional dosage forms. The $t_{max}$ is the time after administration of a drug when the maximum plasma concentration is reached; that is when the rate of absorption equals the rate of elimination. The $C_{max}$ following oral and subcutaneous administration of traditional immediate release dosage forms of MTX are similar (Hoekstra et al., *J Rheumatol*, 31 645-648 (2004)).

Importantly, it has been observed that keeping the $C_{max}$ of MTX low reduces the incidence of the side effects of MTX administration to extremely low levels. It has been found that if $C_{max}$ is kept at 0.16 µmol/l or lower, the incidence of side effects significantly decreased. (Shoda et al., *Mod. Rheumatol*, 17: 311-316, 2007). A slow-release preparation which provides MTX in a low $C_{max}$ in addition to a therapeutically effective AUC (plasma concentration) over a prolonged period of time would provide significant benefits.

The embodiments of the present application provide such significant benefits. The instant MTX MVL formulations provide slow-release formulations which have a low $C_{max}$ of MTX and a therapeutically effective AUC that reduces the incidence of side effects to extremely low levels.

The instant MTX MVL formulations also provide the AUC necessary to maintain the efficacy of MTX. Thus, the slow-release MTX MVL formulations described in the present application achieve the AUC necessary for MTX to function as a first-line DMARD, while providing a $C_{max}$ low enough to reduce the incidence of the side effects of MTX use to extremely low levels.

In particular, the MVL used herein to deliver the MTX are defined as liposomes containing multiple non-concentric chambers within each liposome particle, resembling a "foam-like" matrix. Such particles are to be distinguished from multilamellar vesicles (MLV), also known as multilamellar liposomes, which enclose concentric aqueous compartments. A further distinct particle is the unilamellar vesicle (ULV), also known as a unilamellar liposome, which encloses a single internal aqueous compartment.

SUMMARY OF THE INVENTION

The present embodiments provide a formulation comprising multivesicular liposomes containing an amount of methotrexate, wherein administration of a single dose of said formulation to a subject in need thereof results in a $C_{max}$ of said methotrexate of from 5% to 50% of the $C_{max}$ of immediate release dosage forms of methotrexate, and wherein the duration of said methotrexate in the subject is from about 1 to about 30 days. In some embodiments, the multivesicular liposome further comprises a salt of methotrexate. In some embodiments, the salt is sodium. In other embodiments, the salt is potassium. In additional embodiments, the salt comprises an organic base as a counter ion. In some embodiments, the duration of methotrexate in the subject is from about 1 to about 7 days.

In other embodiments, the multivesicular liposome further comprises a Folate. In some embodiments, the multivesicular liposome further comprises cholesterol, one or more phospholipids or one ore more salts thereof, and one or more triglycerides. In certain embodiments, the phospholipid is a phosphatidyl choline, a phosphatidyl glycerol or salts thereof, or a combination of these. In other embodiments, the phosphatidyl glycerol is DPPG (dipalmitoylphosphatidylglycerol or 1,2-dipalmitoyl-sn-glycero-3-phospho-rac-(1-glycerol)). In additional embodiments, the phosphatidyl choline is DEPC (Dierucoylphosphatidylcholine or 1,2-dierucoyl-sn-glycero-3-phosphocholine). In other embodiments, the multivesicular liposome further comprises DOPC (dioleylphosphatidylcholine or 1,2-dioleoyl-sn-glycero-3-phosphocholine). In another embodiment, the triglyceride is triolein, tricaprylin, or a combination of the two. IN further embodiments, the multivesicular liposome further comprises lysine.

In some embodiments, the duration of the methotrexate plasma levels is about 1 day. In other embodiments, the duration of the methotrexate plasma levels is about 2 days. In another embodiment, the duration of the methotrexate plasma levels is about 3 days. In another embodiment, the duration of the methotrexate plasma levels is about 4 days. In another embodiment, the duration of the methotrexate plasma levels is about 5 days. In another embodiment, the duration of the methotrexate plasma levels is about 6 days. In further embodiments, the duration of the methotrexate plasma levels is about 7 days.

In another embodiment, the formulation is stable for at least two years.

In some embodiments, the formulation can be delivered through needle gauges of 27-31G.

Another embodiment provides a method for treating autoimmune diseases comprising, administering the instant MTX-MVL formulations to a subject in need thereof. In some embodiments, the autoimmune disease is rheumatoid arthritis. In other embodiments, the autoimmune disease is psoriasis. In further embodiments, the autoimmune disease is lupus. In another embodiment, the autoimmune disease is scleroderma. In another embodiment, the autoimmune disease is Sjogren's syndrome. In other embodiments, the autoimmune disease is Goodpasture's syndrome. In some embodiments, the autoimmune disease is Wegener's granulomatosis. In additional embodiments, the autoimmune disease is polymyalgia rheumatica. In another embodiment, the autoimmune disease is Guillain-Barre syndrome. In further embodiments, the autoimmune disease is Crohn's disease.

In some embodiments, the multivesicular liposome further comprises a sodium or potassium salt of methotrexate. In further embodiments, the multivesicular liposome further comprises lysine.

In some embodiments, the multivesicular liposome further comprises a Folate. In other embodiments, a Folate is administered. In further embodiments, a Folate encapsulated in a MVL that does not contain MTX is administered.

Also provided is a method the multivesicular liposome further comprises cholesterol, a phospholipid or one or more salts thereof, and tricaprylin. In some embodiments, the multivesicular liposome further comprises DOPC and triolein. In additional embodiments, the multivesicular liposome further comprises DEPC. In other embodiments, the multivesicular liposome further comprises lysine.

In some embodiments, the duration of the methotrexate plasma levels is about 1 day. In other embodiments, the duration of the methotrexate plasma levels is about 2 days. In another embodiment, the duration of the methotrexate plasma levels is about 3 days. In another embodiment, the duration of the methotrexate plasma levels is about 4 days. In another embodiment, the duration of the methotrexate plasma levels is about 5 days. In another embodiment, the duration of the methotrexate plasma levels is about 6 days. In further embodiments, the duration of the methotrexate plasma levels is about 7 days.

In other embodiments, administration of the formulation comprises injecting said subject with MTX-MVL formulations described herein. In some embodiments, the injection is subcutaneous. In other embodiments, the injection is intramuscular. In other embodiments, the injection is intradermal. In further embodiments, the injection is intratumoral. In other embodiments, the injection is intraspinal. In one embodiment, the injection is administered every 5 to 7 days. In another embodiment, the injection is administered once a week.

Another embodiment provides a method for treating cancer comprising administering the instant MTX-MVL formulations wherein said formulation is administered no more than every two days and no less than every four days to a subject in need thereof. In some embodiments, the cancer is a solid tumor cancer. In other embodiments, the cancer is gestational trophoblastic tumors, breast cancer, head and neck cancer, or lung cancer. In further embodiments, the cancer is gestational trophoblastic tumors (chorioadenoma destruens, choriocarcinoma, or hydatidform mole). In some embodiments, the cancer is a blood born cancer. In further embodiments, the blood born cancer is acute lymphoblastic leukemia, non-Hodgkin lymphoma, mycosis fungoides, or osteosarcoma.

In some embodiments, the multivesicular liposome further comprises a Folate. In other embodiments, a Folate is administered. In further embodiments, a Folate encapsulated in a MVL that does not contain MTX is administered.

In some embodiments, the multivesicular liposome further comprises a sodium or potassium salt of methotrexate. In other embodiments, the multivesicular liposome further comprises cholesterol, a phospholipid or one ore more salts thereof, and tricaprylin. In additional embodiments, the multivesicular liposome further comprises DOPC. In another embodiment, the multivesicular liposome further comprises lysine.

In some embodiments, administration of the formulation comprises injecting said subject with said formulation. In other embodiments, the injection is subcutaneous. In another embodiment, the injection is administered every 2 days.

Another embodiment provides instant MTX-MVL formulations substantially free of cyclodextrin compounds, and preferably free of cyclodextrin compounds.

DETAILED DESCRIPTION

Figure 1:
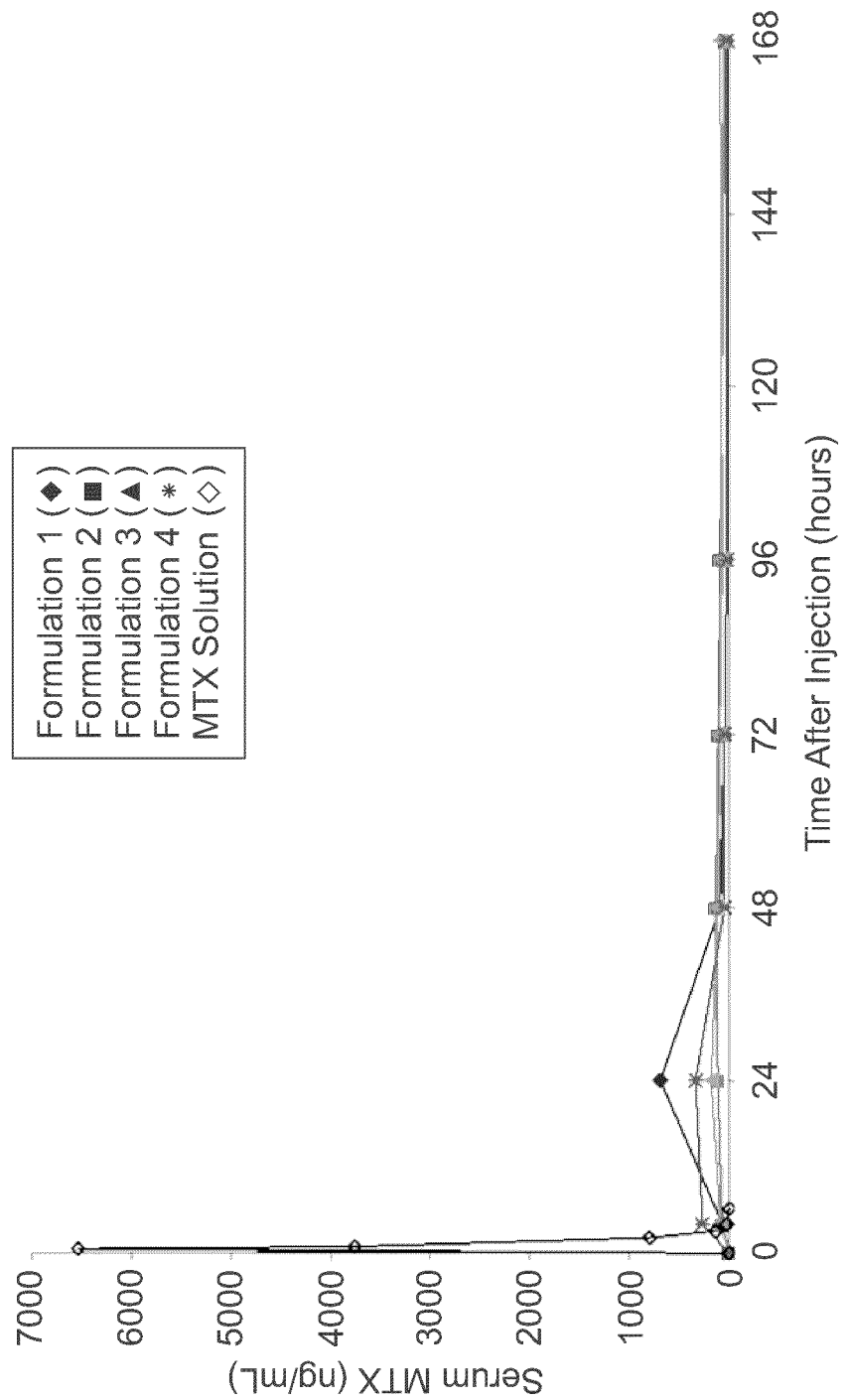
FIG. 1 is a graph showing the plasma concentrations following subcutaneous injection of an MTX control solution and examples of the instant MVL MTX formulations.

The present embodiments provide a formulation comprising multivesicular liposomes containing an amount of methotrexate, wherein administration of a single dose of said formulation to a subject in need thereof results in a $C_{max}$ of said methotrexate between 5% and 50% of the $C_{max}$ of immediate release dosage forms of methotrexate, and wherein the duration of said methotrexate in the subject is from about 1 to about 30 days.

The present embodiments also provide a method for treating autoimmune diseases comprising, administering a formulation described herein to a subject in need thereof.

The present embodiments further provide a method for treating cancer comprising administering a formulation described herein, wherein said formulation is administered no more than every two days and no less than every four days to a subject in need thereof.

Unless otherwise defined, all technical and scientific terms used herein have the same meaning as commonly understood by one of ordinary skill in the art to which this present application belongs. Although methods and materials similar to those described herein can be used in the practice or testing of the present application, suitable methods and materials are described below. All publications, patent applications, patents, and other references mentioned herein are incorporated in the application by reference in their entirety. In addition, the materials, methods, and examples are illustrative only and not intended to be limiting.

In particular, the term AUC means plasma area under the curve of a plasma concentration versus time plot; the term $C_{max}$ is a pharmacokinetic term and means the maximum plasma concentration of the drug; the term $t_{max}$ means the time to $C_{max}$; the term $C_{max}$-relating side effects means side effects which are related to the plasma concentration including but not limited to nausea, vomiting, abdominal discomfort, taste disturbance, anorexia, dyspepsia, and diarrhea; the term MTX means methotrexate and its salts and solutes as discussed below; the term $t_{1/2}$ is the time it takes half the MTX to clear the plasma; the term MVL means multivesicular liposome; the term DMARD means disease-modifying antirheumatic drug; the term "duration of MTX plasma levels" means the time between administration and time that the cumulative plasma AUC reaches 90% of the AUC of the cumulative AUC at infinite time; the term "immediate release dosage form" means that there is nothing in the dosage to retard the release of the drug; the term "drug holiday" is the period between administrations when the drug has essentially cleared the patients' plasma. The term "subject in need thereof" means mammals, and including humans. The term "cyclodextrin compounds" means one or more compounds chosen from the group consisting of alpha, beta, and gamma cyclodextrin or derivatives thereof. One of such derivatives includes 2-hydroxypropyl-β-cyclodextrin. Other derivatives include the sulfobutyl ether alpha, beta or gamma cyclodextrin.

Autoimmune diseases arise from an overactive immune response of the body against substances and tissues normally present in the body. The immune system mistakes some part of the body as a pathogen and attacks it. This may be restricted to certain organs or involve a particular tissue in different places. The treatment of autoimmune diseases is typically performed with immunosuppression—medication which decreases the immune response. The term "autoimmune diseases" as used herein includes, but is not limited to Crohn's disease, dermatomyositis, diabetes mellitus type 1, Goodpasture's syndrome, Graves' disease, Guillain-Barre syndrome, Hashimoto's disease, idiopathic thrombocytopenic purpura, lupus, mixed connective tissue disorder, myasthenia gravis, narcolepsy, pemphigus vulgaris, pernicious anaemia, polymyositis, primary biliary cirrhosis, psoriasis, rheumatoid arthritis, Sjogren's syndrome, temporal arteritis, ulcerative colitis, vasculitis, and Wegener's granulomatosis.

One embodiment of the present application provides MTX MVL formulations containing MTX and salts thereof to treat autoimmune diseases, particularly RA and psoriasis. The instant MTX MVL formulations have a $C_{max}$ of MTX that is generally between 5% and 50% of the $C_{max}$ of immediate release dosage forms of MTX. In the immediate release dosage form, MTX has a very high and very early $C_{max}$ and then quickly drops below the limit of quantification ("LOQ") within 24 hours. As discussed above, administration of the instant MTX MVL formulations keep the $C_{max}$ of MTX low which reduces the incidence of the side effects of MTX use to extremely low levels. Preferably the $C_{max}$ remains at or below 0.16 µmol/L for the treatment of autoimmune diseases. The instant MTX MVL formulations of the present application provide a sustained AUC at a therapeutic concentration of MTX with a duration from about 1 to about 30 days. Preferably the duration is from about 1 to about 7 days. For the treatment of autoimmune disease, the duration is preferably from 1 to 5 days.

MTX has also been used to treat certain cancers and cancer conditions. The instant MTX MVL formulations can be used to treat solid tumor cancers. Such cancers, as discussed herein, include, but are not limited to, certain types of gestational trophoblastic tumors, including chorioadenoma destruens, choriocarcinoma, and hydatidform mole, as well as breast cancer, head and neck cancer, and lung cancer. The instant MTX MVL formulations can also be used to treat blood borne cancers. Such cancers, as discussed herein, include, but are not limited to, acute lymphoblastic leukemia, non-Hodgkin lymphoma, mycosis fungoides, and osteosarcoma. The instant MTX MVL formulations can also be used for direct delivery to tumors (e.g., intraspinal for delivery to the cerebrospinal fluid or by intratumoral delivery). In some embodiments, the formulations and methods of the present embodiments are directed to the treatment of menningeal leukemia by intrathecal injection.

As discussed above, the MTX MVL formulations of the present application have a plasma $C_{max}$ that is between 5% and 50% of the $C_{max}$ of immediate release dosage forms of MTX for the treatment of autoimmune diseases. For the systemic treatment of cancer, a significantly higher $C_{max}$ is generally used relative to autoimmune diseases. Nonetheless, reduced side effects can be achieved by reducing the $C_{max}$ relative to the administration of the same MTX dose administered with an immediate release dosage form MTX. The MTX MVL formulations of the present application for the systemic treatment of cancer also provide a sustained exposure at a therapeutic AUC of MTX with the duration from about 1 to about 30 days. In some embodiments, the duration is from about 1 to about 7 days. Some cancers can be treated locally. For example, meningeal leukemia is treated with an intrathecal injection of MTX dosed at 12 mg/sq m (max of 15 mg) using a 1 mg/mL solution every 2-5 days. Another example would be one or more tumors that can receive an intratumoral injection. In these local treatments, the plasma concentration is irrelevant. Rather, the local concentration is of importance. The instant MVL MTX formulations are useful in these local treatments due to the fact that it provides a sustained local level of drug. This provides efficacy and reduces the number of injections which are necessary, thus providing patient and care giver convenience.

For autoimmune diseases, in addition to providing MTX MVL formulations with a $C_{max}$ that is between 5% and 50% of the plasma $C_{max}$ of immediate release dosage forms of MTX, surprisingly the instant MTX MVL formulations provide the same or better efficacy than the immediate release dosage forms at the same MTX dose. The efficacy of MTX is not related to the $C^-_{max}$ of MTX but is directly correlated with the AUC. Accordingly, the MVL formulations of the present application have an AUC that is equivalent or better than that of immediate release dosage forms of MTX as described above. Preferably, the instant MTX MVL formulations provide the same AUC as subcutaneous immediate release dosage forms of MTX. This AUC can be greater if the reduced side effects allow higher dosing. Furthermore, the instant formulations and methods of treatment using the formulations can be substantially cyclodextrin free, and preferably cyclodextrin free. Surprisingly, the advantageous effects described herein for the instant formulations and methods have been achieved without the use of cyclodextrin compounds. For instance, the instant formulations and methods achieved long duration times without the MTX being complexed with cyclodextrin compounds.

Furthermore, the instant formulations and methods of treatment using the formulations can be substantially cyclodextrin free, and preferably cyclodextrin free. MTX release from MVL formulations containing MTX complexed with hydroxylpropyl-beta-cyclodextrin has previously been reported by Kim et al. (Cancer Chemother. Pharmacol. 33: 303-306 (1994); U.S. Pat. No. 5,759,573) following subcutaneous administration to rodents. The formation of the inclusion complex resulted in a reduction in the rate of release (see col. 4:27-34; col. 5:14-19). Surprisingly, the advantageous effects described herein for the instant formulations and methods have been achieved without the use of cyclodextrin compounds. For instance, the instant formulations and methods achieved long duration times without the MTX being complexed with cyclodextrin compounds.
Methotrexate The present embodiments use MTX and its salts, hydrates, and solutes, whether crystalline or amorphous, thereof encapsulated in MVL. Such salts include sodium, potassium, lysine, arginine, and other pharmaceutically acceptable mono or divalent basic addition salts. The term "MTX" includes any and all such forms as used herein. The instant MTX MVL formulations and methods exhibit their desirable properties without the need for complexing the MTX with cyclodextrin or its derivatives.
Multivesicular Liposomes The formulations of the present embodiments employ MTX encapsulated multivesicular liposomes (MTX-MVL) which encapsulate and provide modulated and sustained release of the MTX described above. The MVL are made by the following process.

A "water-in-oil" type emulsion containing MTX is formed from two immiscible phases, a lipid phase and a first aqueous phase. The lipid phase is made up of at least one amphipathic lipid and at least one neutral lipid in a volatile organic solvent. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capabilities by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen form a wide range of lipids having a hydrophobic region and a hydrophilic region in the same molecule. Suitable amphipathic lipids are zwitterionic phospholipids, including phosphaitdycholines, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, stearylamine, and the like. Preferred amphipathic lipids include dioleyl phosphatidyl choline (DOPC), dierucoylphosphatidylcholine (DEPC), and dipalmitoylphosphatidylglycerol (DPPG). Certain embodiments of amphipathic lipids for the instant MTX MVLs used to treat autoimmune diseases such as rheumatoid arthritis as well as cancer include DOPC and DEPC in conjunction with DPPG.

Suitable neutral lipids are triglycerides, propylene glycol esters, ethylene glycol esters, and squalene. Examples of triglycerides useful in the instant formulations and methods are triolein (TO), tripalmitolein, trimyristolein, trilinoelin, tributyrin, tricaproin, tricaprylin, and tricaprin. The fatty chains in the triglycerides useful in the present application can be all the same, or not all the same (mixed chain triglycerides), including all different. Both propylene glycol esters can be mixed diesters of caprylic and capric acids. In particular, neutral lipids, for instance, triolein, can be increased to a percentage range from about 0.01% to about 20% in order to decrease the $C_{max}$ yet still retain the advantage offered by these formulations, especially in the treatment of the autoimmune diseases. In particular, the percentage range for triolein is from about 1% to 2% of the neutral lipids such as tricaprylin used in the instant formulations regarding the molar ratios. Additionally, cholesterol or plant sterols are included in the instant MVLs.

Many types of volatile organic solvents can be used in the present application, including ethers, esters, halogenated ethers, hydrocarbons, halohydrocarbons, or freons. For example, diethyl ether, chloroform, methylene chloride, tetrahydrofuran, ethyl acetate, and any combinations thereof are suitable for use in making the formulations.

Optionally, but highly desirably, other components are included in the lipid phase. Among these are antioxidants, antimicrobial preservatives, cholesterol or plant sterols.

The first aqueous phase includes MTX, a base, and an osmotic agent (e.g. sodium chloride, sucrose, glucose, fructose or mixtures thereof). The lipid phase and first aqueous phase are mixed by mechanical turbulence, such as through use of rotating or vibrating blades, shaking, extrusion through baffled structures or porous pipes, or by ultrasound to produce a water-in-oil emulsion. Thus, the MTX of the present application is encapsulated directly in the first step of MVL manufacture.

The water-in-oil emulsion is then dispersed into a second aqueous phase by means described above, to form solvent spherules suspended in the second aqueous phase, a water-in-oil-in-water emulsion is formed. The term "solvent spherules" refers to a microscopic spheroid droplet of organic solvent, within which are suspended multiple smaller droplets of aqueous solution. The resulting solvent spherules therefore contain multiple aqueous droplets with the MTX dissolved therein. The second aqueous phase can contain additional components such as glucose, sucrose, and/or lysine.

The volatile organic solvent is then removed from the spherules, for instance by surface evaporation from the suspension. When the solvent is substantially or completely evaporated, MVL are formed. Gases which can be used for the evaporation include nitrogen, argon, helium, oxygen, hydrogen, and carbon dioxide. Alternately, the volatile solvent can be removed by sparging, rotary evaporation, diafiltration or with the use of solvent selective membranes.

In some embodiments ranges of lipids in the instant MTX MVL formulations can be as follows: cholesterol can be from about 5 to about 80 mM; phosphatidylcholine can be from about 5 to about 50 mM; tricaprylin can be from about 5 to about 80 mM; triolein can be from about 0 to about 8 mM; and phosphatidylglycerol can be from about 0 to about 15 mM. DPPG is optional, as is the use of other charged lipids. For the treatment of cancer, a longer duration than RA is preferable. This can be achieved by increasing the amount of triglyceride, by increasing the ratio of long to short chain triglycerides by using a longer chain phosphatidylcholine or by increasing the cholesterol concentration.

Methods of making the instant MVL formulations can also be found in Hartouian et al., U.S. Publication No. 2007-0235889 and Hartouian et al., WO99/25319 (PCT/US98/24261) which is incorporated by reference in the present application in its entirety.

Folates

In further embodiments, folic acid, folinic acid (leucovorin), an active enantiomer of either, or their salts (collectively referred to as Folates) can be used in combination with MTX to reduce side effects associated with MTX, particularly with regard to the gastrointestinal tract, liver, and blood cells (Prey and Paul, *Brit J. Dermatol.*, 160:622-628 (2009). The dose and dosing frequency of the Folates can vary from about 1 to about 27.5 mg/week (Oritz et al., *J. Rheumatol*, 25 (1998) 36-43). Typical doses may be about 2.5 to about 5 mg/week or about 1 to about 2 mg/day (Hoekstra et al., *Ann Rheum Dis*, 62:423-426 (2003).

The instant MTX-MVL formulations can use a Folate to decrease Cmax-related side effects such as nausea and vomiting using the sustained release properties of the MVL as well as side effects which can be diminished by Folates. The Folate can be included in the instant formulation, for example, in one or more of the following ways. First, the Folate could be in the external solution (unencapsulated). Second, the Folate could be included in the same first aqueous solution as the MTX, and thus, would be released at roughly the same rate as the MTX following administration. Third, the Folate and MTX can be formulated in heterovesicular liposomes (see Kim, U.S. Pat. No. 5,422,120, Jun. 6, 1995). Fourth, the Folate and MTX can be included in separate populations of MVL particles. Finally, the Folate and MTX can be included as any combination of the above.

In the fourth case, these separate populations can have the same lipid compositions providing essentially the same rate of release, or they can have different lipid compositions providing different rates of release in order to optimize the side effect, sparing effectiveness of the Folate. The separate populations can be combined in one container, in separate containers, or in a two chamber container designed to mix the two just prior to or during administration. In the case of two separate containers, the two can be administered at the same or at different times.

Methods of Administration

The MTX formulations discussed above can be administered by injection, and more specifically by subcutaneous, intradermal, or intramuscular injection on a weekly basis for systemic use including the treatment of autoimmune diseases such as RA. They may also be delivered locally (e.g. intraspinal or intratumoral) in the treatment of cancer. For RA, the term "therapeutically effective" as it pertains to the compositions of this present application means that a MTX present in the first aqueous phase within the MVL is released in a manner sufficient to achieve an effective AUC of MTX, such AUC levels from about 1000-5000 mcg/L-hr. Much higher levels will be used for the systemic treatment of cancers. When local delivery is used for the treatment of cancers, the amount delivered can be significantly reduced. Exact dosages will vary depending on patient factors such as age, sex, general condition, and the like. Those of skill in the art can readily take these factors into account and use them to establish effective therapeutic concentrations without resort to undue experimentation.

For the treatment of autoimmune diseases, the instant MTX MVL formulations preferably would be injected subcutaneously one time per week. In one example, duration of the MTX is from about 1 to about 5 days. Thus, the instant MTX MVL formulations provide an approximately two day drug holiday. This holiday reduces the side effects related to MTX.

For the treatment of cancer, the instant MTX MVL formulations would be injected no more than every two days, and in another embodiment injected subcutaneously every seven days. The treatment will be repeated for several courses of treatment. To reduce side effects due to the large doses used in cancer, the patient may also be given a "leucovorin rescue" (Link M P, Goorin A M, Miser A W, et al.; N. Eng. J. of Med. 1986; 314 (No. 25): 1600-1606) or allowed a 7-10 day rest period between treatments. However, the need for leucovorin or rest periods will be diminished due to the low $C_{max}$ release profile with the MVL.

For the treatment of cancer, a guideline ratio for human dosage forms of 1:30 is given for the conversion of 100 mg/kg body weight to 37 mg/m$^2$ body surface area in adult humans. The conversion factor actually varies between 1:20 and 1:40, depending on age and body build.

For the treatment of autoimmune diseases such as RA, a new patient would receive a dose of the instant MTX MVL formulations that had a total amount of 2-5 mg of MTX, with titration of 2-5 mg/wk up to 25-35 mg/wk. Such administration is intended to provide delivery of MTX over a period of several hours to several days, and for example, up to a period of about five days. Such an MTX MVL formulation, relative to an immediate release injectable or oral formulation, reduces side effects as enumerated above, retains the AUC of a subcutaneous injection of an immediate release MTX formulation, and improves $C_{max}$ versus current immediate release oral MTX administrations with equal or better efficacy as judged by the American College of Rheumatology scoring system. See Felson et al., *Arthritis & Rheumatism*, Vol. 38, No. 6, June 1995.

For the treatment of cancer, the MVL encapsulated MTX formulations are administered the same way as for autoimmune diseases but with higher doses. Again, the MTX formulations discussed above can be administered by injection, and more specifically by subcutaneous, intradermal, or intramuscular injection on a weekly basis for systemic use in the treatment of cancer. They may also be delivered locally (e.g. intraspinal) or intratumoral.

Nonlimiting Disclosure and Incorporation By Reference

While certain therapeutic agents, compositions and methods have been described with specificity in accordance with certain embodiments, the following examples serve only to illustrate the compositions and methods of the invention and are not intended to limit the same. Each of the references and the like recited in this application are incorporated herein by reference in its entirety.

EXAMPLES

The instant MVL MTX formulations were prepared in a manner similar to that reported by Kim et al. (*Biochim Biophys Acta,* 728 (1983) 339-348). An aqueous solution containing MTX, sodium hydroxide and sucrose was emulsified with chloroform solution containing DOPC or DEPC, DPPG, tricaprylin and/or triolein, and cholesterol, resulting in a water-in-oil (W/O) emulsion. The W/O emulsion was then emulsified in a second aqueous solution containing lysine and sucrose to produce a W/O/W emulsion. The W/O/W emulsion was then was stirred at 37° C. under a nitrogen stream to remove the chloroform by evaporation. The resulting particles were centrifuged, and the supernatant replaced with normal saline. After washing, the particles were diluted into normal saline to yield a product with approximately a 50% packed particle volume (PPV). PPV is the fraction of the total formulation volume taken up by the MVL particles.

The compositions of the solutions used to prepare four formulations by the above method are listed in Table 1 below. The resulting particles had median diameters ranging from 13-15 microns and a potency of approximately 25 mg/mL.

As used in Table 1 below for particle size distribution, d10 means 10% or less of the particles have the diameter identified in the table. d50 means 50% or less of the particles have the diameter identified in the table. d90 means 90% or less of the particles have the diameter identified in the table. The "span" is calculated by subtracting d90 from d10 and dividing that result by d50.

As used in Table 1, "% Free" means the percent of MTX outside of the MVL and PPV means packed particle volume.

TABLE 1

| | Component | Formulation 1 | Formulation 2 | Formulation 3 | Formulation 4 |
|---|---|---|---|---|---|
| 1st Aqueous Solution | MTX (mg/mL) | 61.75 | 61.75 | 61.75 | 61.75 |
| | NaOH (mM) | 286.6 | 286.6 | 286.6 | 286.6 |
| | Sucrose (mg/mL) | 24.4 | 24.4 | 24.4 | 24.4 |
| | pH | 7.42 | 7.42 | 7.42 | 7.42 |
| | Osmolality (mOsm) | 304 | 304 | 304 | 304 |
| Lipid Combo | Tricaprylin (mM) | 40.0 | 40.0 | 40.0 | 20.0 |
| | Cholesterol (mM) | 40.0 | 40.0 | 40.0 | 20.0 |
| | DPPG-Na+ (mM) | 5.6 | 5.6 | 5.6 | 2.8 |
| | DEPC (mM) | 0.0 | 26.4 | 0.0 | 0.0 |
| | DOPC (mM) | 26.4 | 0.0 | 26.4 | 13.2 |
| | Triolein (mM) | 0.0 | 0.0 | 0.8 | 0.0 |
| 2nd Aqueous solution | Lysine (mM) | 20 | 20 | 20 | 20 |
| | Dextrose•H2O | n/a | n/a | n/a | n/a |

TABLE 1-continued

| | Component | Formulation 1 | Formulation 2 | Formulation 3 | Formulation 4 |
|---|---|---|---|---|---|
| | (mM) | | | | |
| | Sucrose | 8.6% | 8.6% | 8.6% | 8.6% |
| | pH | 10.15 | 10.15 | 10.15 | 10.15 |
| | Osmolality (mOsm) | 300 | 300 | 300 | 300 |
| Particle Size Distribution | d10 | 6.8 | 6.7 | 6.8 | 7.3 |
| | d50 | 13.4 | 13.7 | 13.1 | 14.7 |
| | d90 | 25.7 | 27.3 | 25.3 | 31.8 |
| | Span | 1.405 | 1.500 | 1.406 | 1.672 |
| Analytical Results | Total Potency (mg/mL) | 24.8 | 24.0 | 24.6 | 26.8 |
| | % Free | 0.2% | 0.2% | 0.2% | 0.9% |
| | PPV % | 53% | 52% | 57% | 54% |

The final composition of Formulation 1 would have an approximate final composition as given in the table below.

TABLE 2

| Component | Formulation 1 |
|---|---|
| Methotrexate API | 55.0 mM (25 mg/mL) |
| DOPC | 14.52 mM |
| DPPG | 3.08 mM |
| Cholesterol | 22 mM |
| Tricaprylin | 22 mM |
| NaOH | QS to pH 7.4 (ca. 131 mM) |
| Sucrose | 38.7 mM |
| NaCl | 69.3 mM |

A pharmacokinetic (PK) study was performed in rats, comparing MTX solution control against four different formulations of MVL-encapsulated MTX at a dose level of 10 mg/kg. Male Sprague Dawley rats weighing 280-320 g received subcutaneous injections of either MTX solution or one of the MVL-encapsulated MTX formulations. The injections were made on the left lateral hind limb of each rat using 1 mL syringes fitted with 25G needles. Each treatment group contained 3 rats. Appropriate dilutions with sterile saline solution were performed to provide a dose of 10 mg/kg of MTX per rat, assuming an average rat weight of 300 g (final injection volume of 200 uL). Rats were ordered by pre-dose weight and then randomized into the different treatment groups.

Serum MTX analysis was performed to measure MTX in serum using a liquid-liquid extraction (LLE) HPLC method performed by an Agilent 1200 Series system produced by Agilent Technologies headquartered in Santa Clara, Calif. A 100 μL volume of rat serum was mixed with 300 μL of acetonitrile solution containing 1.1% formic acid (w/v) in a 1.5-mL Eppendorf tube. The deproteinization was carried out by vortexing for 1 minute, followed by centrifugation at 13,000 g for 5 minutes. The entire supernatant was transferred into a 1.5-mL microcentrifuge tube with screw cap. Acetonitrile was cleaned out by mixing 500 μL of chloroform with the supernatant. The tube was vortexed for 1 minute and then centrifuged at 13,000 g for 3 minutes. A 40 μL volume of the top aqueous portion was collected into a 100-μL vial insert for HPLC sample injection.

The HPLC system was equipped with a detector set at 302 nm and a 2.1-mm×250-mm Supelcosil LC-18-S with 5-μm particle size column. The mobile phase consisted of 102 mM sodium phosphate (dibasic), 32.5 mM citric acid, and 10% (v/v) acetonitrile (pH~6.0). The flow rate was 0.6 mL/min, column temperature 35° C., and injection volume 20 μL. An MTX standard curve was prepared by spiking 6 different concentrations of MTX (22.7-727.1 ng/mL) into MTX-free rat serum. The MTX in each spiked standard was extracted using the same sample preparation method above.

Figure 2:
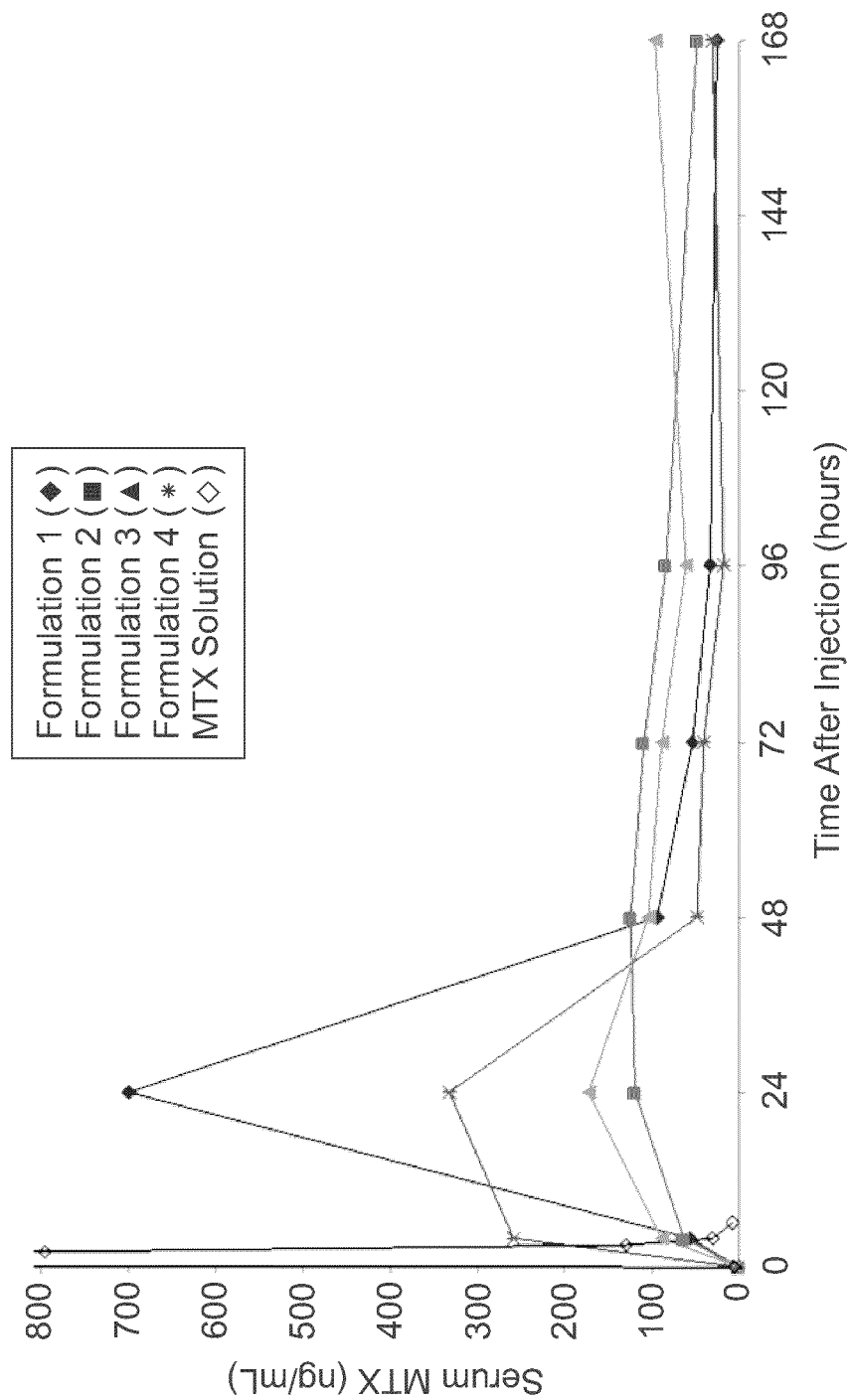
FIG. 2 is the modified graph of FIG. 1 with an altered y-axis showing the plasma concentrations following subcutaneous injection of an MTX control solution and examples of the instant MVL MTX formulations.

As shown in FIG. 1, the methotrexate solution control reached a very high and very early plasma $C_{max}$, dropping just as quickly to below LOQ within 24 hours. For clarity, FIG. 2 represents the same data with an altered y-axes scale, truncating the $C_{max}$ of the MTX solution. All of the groups receiving MVL-encapsulated MTX formulations successfully showed sustained release. That is they surprisingly produced acceptable duration, as well as acceptable $C_{max}$ for reducing side effects. These PK results demonstrate that it is possible to modulate the release rate by varying lipid composition of the MVL-encapsulated MTX formulations. Thus the change in lipid composition of the instant formulations can include modifying the total amount of amphipathic lipid as well as the neutral lipid, the addition or removal of a specific lipid (e.g., the addition of TO), and the substitution one of lipid for another (e.g., DEPC versus DOPC). Examples of how triglyceride levels might be modified are provided in Willis, U.S. Pat. No. 5,891,467, issued on Apr. 6, 1999. Willis was not necessarily predictive of the advantages of the instant embodiments. Increasing the chain length of the phosphatidylcholine has previously been shown to provide an increase in the efficiency of encapsulating a compound (See Ye et al., U.S. Pat. No. 6,171,613, issued Jan. 9, 2001). Ye was not predictive of the advantages of the instant embodiments. For MTX, the data in FIGS. 1 and 2 demonstrate that increasing the chain length increases the duration.

FIGS. 1 and 2 show that the Formulation 1 had most of its release within the first 48 hours and a maximum serum concentration ($C_{max}$) of about 1.5 umol/L. Reducing the amount of lipids in the MVL formulations by half, Formulation 4 gave a similar release profile, except it is shifted to the left, giving a shorter duration and an earlier time to $C_{max}$. Adding 2% TO to the Formulation 3 significantly lowered the $C_{max}$ and greatly extended the duration. Substituting the DOPC of Formulation 1 with DEPC of Formulation 2 gave a similar and even more profound effect, creating a release profile that approximated a zero-order release rate. By using these or similar approaches, it is possible to modify the resulting PK profile of the instant MVL MTX formulations.

Additional PK studies on Formulations 1 and 2 were performed as above, including some at reduced doses of MTX. The PK parameters from these studies are summarized below. As can be seen, the $C_{max}$ is significantly reduced relative to the MTX immediate release solution. The $C_{avg}$ is the average plasma concentration over the 7 day time period. Thus, the formulations were of surprisingly long duration and low $C_{max}$ and, thus, the side effects will be low.

TABLE 3

Additional PK studies on Formulations 1 and 2

| Test article | MTX Dose (mg/kg) | Cmax (µmol/L) | Cmax/Cavg | Tmax (hr) | AUC/Dose (µmol-hr/L/mg/kg) |
|---|---|---|---|---|---|
| MTX Solution | 10 | 14.39 | 4.06 | 0.5 | 1.55 |
| Formulation 1 | 10 | 1.54 | 5.03 | 24 | 4.85 |
|  | 5 | 0.55 | 4.18 | 24 | 2.11 |
|  | 2.5 | 0.23 | 3.5 | 12 | 1.97 |
| Formulation 2 | 10 | 0.27 | 1.58 | 48 | 1.68 |
|  | 5 | 0.12 | 1.87 | 72 | 2.52 |
|  | 2.5 | 0.08 | 2.48 | 48 | 2.36 |

Stability

Further, the stability of the instant MTX MVL formulations is acceptable by industry standards. The stability data is shown for lot numbers 1-3 of Formulation 1 in Tables 4-6, below. Properties assessed included drug content, percent of unencapsulated drug (% free), and related substances by compendial RP-HPLC methods, packed particle volume (PPV) which is assessed in a manner analogous to a hematocrit, appearance which is a visual assessment, and particle size which is assessed by laser light scattering. At refrigerated temperatures (5° C.), no significant changes are observed through 12 months. Likewise, at 25° C., no significant changes are observed through 3 months.

TABLE 4

MVL-MTX (lot #1, Formulation 1) during normal and elevated temperature storage

| Temp | Time | Content (mg/mL) [% initial] | % Free | PPV % | Imp B % | Imp C % | Particle Size (Vol wt'd diameter, µm) d10 | d50 | d90 |
|---|---|---|---|---|---|---|---|---|---|
|  | Initial | 23.2 | 0.38 | 52 | 0.025 | 0.050 | 7.7 | 15.4 | 30.5 |
| 5° C. | 1M | 23.5 [101] | 0.35 | 52 | 0.029 | 0.059 | 7.3 | 14.8 | 30.4 |
| 5° C. | 12M | 23.3 [1.00] | 1.01 | 50 | 0.039 | 0.136 | 7.8 | 15.8 | 31.4 |
| 25° C. | 1M | 23.8 [103] | 0.42 | 50 | 0.035 | 0.129 | 7.5 | 15.0 | 28.8 |
| 25° C. | 3M | 23.6 [102] | 0.86 | 50 | 0.049 | 0.272 | 7.7 | 15.3 | 28.8 |

TABLE 5

MVL-MTX (lot #2, Formulation 1) during normal temperature storage

| Temp | Time | Content (mg/mL) [% initial] | % Free | PPV % | Imp B % | Imp C % | Particle Size (Vol wt'd diameter, µm) d10 | d50 | d90 |
|---|---|---|---|---|---|---|---|---|---|
|  | Initial | 23.6 | 0.34 | 53 | 0.027 | 0.056 | 7.2 | 14.4 | 28.4 |
| 5° C. | 5M | 24.2 [103] | 0.86 | 51 | 0.03 | 0.11 | 7.1 | 15.4 | 33.1 |

TABLE 6

MVL-MTX (lot #3, Formulation 1) during normal temperature storage

| Temp | Time | Content (mg/mL) [% initial] | % Free | PPV % | Imp B % | Imp C % | Particle Size (Vol wt'd diameter µm) d10 | d50 | d90 |
|---|---|---|---|---|---|---|---|---|---|
|  | Initial | 25.6 | 0.06 | 51 | 0.027 | 0.059 | 7.2 | 14.8 | 28.8 |
| 5° C. | 3M | 26.2 [102] | 0.34 | 50 | 0.040 | 0.115 | 7.1 | 15.4 | 30.0 |
| 5° C. | 6M | 26.3 [103] | 0.20 | 51 | 0.038 | 0.125 | 7.0 | 14.7 | 28.6 |
| 5° C. | 12M | 24.7 [96] | 0.29 | 50 | 0.042 | 0.155 | 8.9 | 14.9 | 24.5 |

Figure 3:
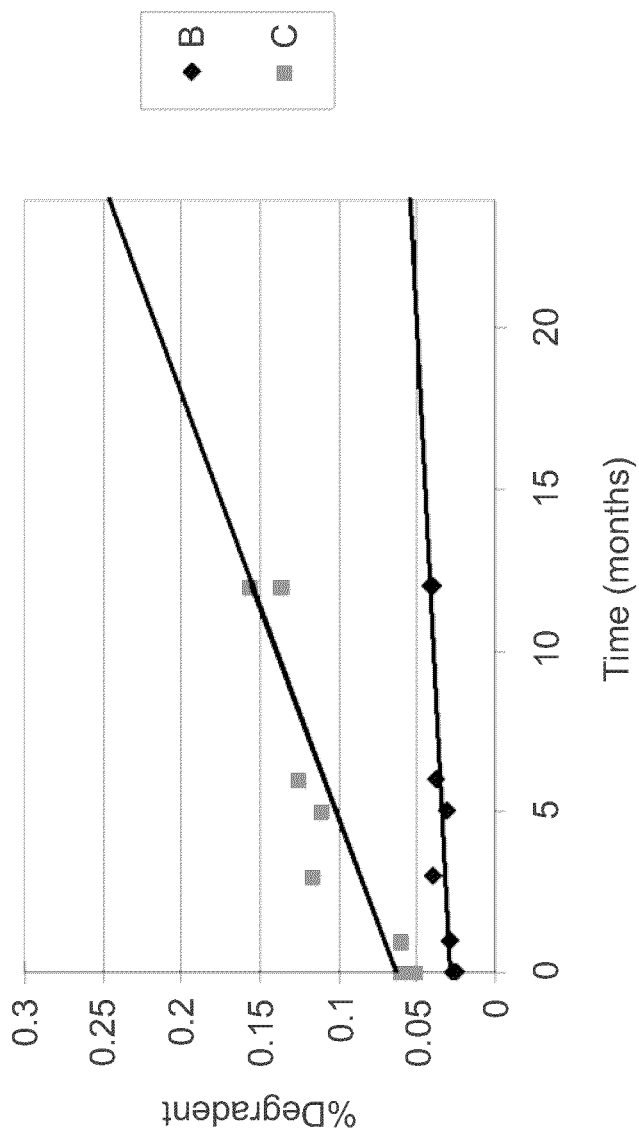
FIG. 3 is a graph showing the percent degradant of Formulation 1 over time.

With regard to related substances, an increase is observed in Impurities B and C which have European Pharmacopeal limits of 0.3 and 0.5%, respectively. Impurities B and C are named impurities in the European Pharmacopeia (EP), and are the only named impurities seen as degradents. Impurity B is (2 S)-2-[[4-[[(2,4-diaminopteridin-6-yl)methyl]amino]benzoyl]amino]pentanedioic acid (4-aminofolic acid, aminopteridine). Impurity C is (2S)-2-[[4-[[(2-amino-4-oxo-1,4-dihydropteridin-6-yl)methyl]methylamino]benzoyl]amino]pentanedioic acid (N-methylfolic acid, methopteridine). Two years of storage is generally accepted as a viable shelf life for pharmaceuticals. By extrapolating the existing data (see FIG. 3), Formulation 1 will likely have levels of Impurities B and C well below the limit at 2 years. Thus, the instant MTX MVL formulations will be stable for at least two years. The instant embodiments include the instant MTX MVL formulations with measured stability, as well as the methods of administration of such formulations for autoimmune diseases and cancer as discussed above.

Syringeability

For injections in general, and particularly in the case of subcutaneous injections which are self-administered by the patient for chronic conditions such as RA, it is desirable to administer the drug with a needle having a small diameter (or high needle gauge). Such needles allow injections with minimal or no pain. Needle gauges of 27-31G are considered narrow and are preferred. Many sustained release injectables cannot be delivered through such narrow needles due to use of either high viscosity (e.g., in situ gelling formulations) or hard and/or relatively large particles (e.g., polymer microparticles). The instant MTX MVL formulations have been found to be readily administrable using such narrow needles. On passing through 27-31G needles, the product characteristics of Formulation 1 are unaffected (see Table 7). These data were generated by using the noted needle attached to a 1-mL syringe, and expressing the formulation at approximately 2 mL/min. The ability to use 27-31G needles provides a unique attribute to this delivery technology, and is likely due to the low viscosity, small particle size, and elastic nature of the particles. The instant embodiments include the instant MTX MVL formulations with measured syringeability, as well as the methods of administration of such formulations for autoimmune diseases and cancer as discussed above.

TABLE 7

Syringeability of Formulation 1

| Depo-MTX sample source | Total Potency Total MTX (mg/mL) | % Free % | PPV PPV % | Particle Size Distribution | | |
|---|---|---|---|---|---|---|
| | | | | d10 (µM) | d50 (µM) | d90 (µM) |
| From glass vial only (No syringe-needle) | 25.13 | 1.1 | 58.5% | 7.5 | 14.0 | 27.7 |
| syringe only, no needle | 24.88 | 0.7 | 58.5% | 7.5 | 14.6 | 27.1 |
| syringe + 27G-1/2" Needle | 25.05 | 0.7 | 58.5% | 7.8 | 15.2 | 28.9 |
| syringe + 28G-1/2" Needle | 24.91 | 0.8 | 57.7% | 7.7 | 15.0 | 28.1 |
| syringe + 29G-1/2" Needle | 24.81 | 0.8 | 58.5% | 7.8 | 15.2 | 28.7 |
| syringe + 30G-1/2" Needle | 25.41 | 0.9 | 58.5% | 7.6 | 14.8 | 27.5 |
| syringe + 31G-5/16" Needle | 24.96 | 1.2 | 57.7% | 7.8 | 15.3 | 29.0 |

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least;" the term "includes" should be interpreted as "includes but is not limited to;" the term "example" is used to provide exemplary instances of the item in discussion, not an exhaustive or limiting list thereof; adjectives such as "known", "normal", "standard", and terms of similar meaning should not be construed as limiting the item described to a given time period or to an item available as of a given time, but instead should be read to encompass known, normal, or standard technologies that may be available or known now or at any time in the future; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A formulation comprising multivesicular liposomes for administration by injection, said multivesicular liposomes comprise an amount of a basic addition salt of methotrexate, one or more amphipathic lipids or salts thereof, one or more neutral lipids, and optionally cholesterol or plant sterols, wherein the formulation is substantially cyclodextrin free, wherein administration of a single dose of said formulation to a subject in need thereof results in a plasma $C_{max}$ of said methotrexate of from 5% to 50% of the plasma $C_{max}$ of immediate release dosage forms of methotrexate, and wherein a duration of said methotrexate in the subject is from about 1 to about 30 days.

2. The formulation as in claim 1, wherein the basic addition salt of methotrexate is a sodium salt.

3. The formulation as in claim 1, wherein the basic addition salt of methotrexate is a potassium salt.

4. The formulation as in claim 1, wherein the basic addition salt of methotrexate comprises an organic base as a counter ion.

5. The formulation as in claim 1, wherein the multivesicular liposome further comprises a Folate to decrease $C_{max}$-related side effects.

6. The formulation as in claim 1, wherein the multivesicular liposome comprises cholesterol, one or more amphipathic lipids or salts thereof, and one or more triglycerides.

7. The formulation as in claim 6, wherein said one or more amphipathic lipids are selected from one or more phosphatidylcholines, one or more phosphatidylglycerols or salts thereof, or combinations thereof.

8. The formulation as in claim 7, wherein the phosphatidylglycerol comprises DPPG.

9. The formulation as in claim 7, wherein the phosphatidylcholine comprises DEPC.

10. The formulation as in claim 7, wherein the phosphatidylcholine comprises DOPC.

11. The formulation as in claim 6, wherein said one or more triglycerides are selected from triolein, tricaprylin, or a combination of the two.

12. The formulation as in claim 1, wherein the multivesicular liposome further comprises lysine.

13. The formulation as in claim 1, wherein the duration of the methotrexate plasma levels is about 1 day to 7 days.

14. The formulation as in claim 1, wherein the formulation is stable for at least two years.

15. The formulation as in claim 1, wherein the formulation can be delivered through needle gauges of 27-31G.

16. The formulation as in claim 1, wherein the concentration of cholesterol in said formulation is from about 5 to about 80 mM in an organic solvent solution that forms a first water-in-oil (w/o) emulsion.

17. The formulation as in claim 7, wherein the concentration of phosphatidylcholines in said formulation is from about 5 to about 50 mM in an organic solvent solution that forms a first water-in-oil (w/o) emulsion.

18. The formulation as in claim 7, wherein the concentration of phosphatidylglycerol in said formulation is from about 0 to about 15 mM in an organic solvent solution that forms a first water-in-oil (w/o) emulsion.

19. The formulation as in claim 11, wherein the concentration of triolein is from about 0 to about 8 mM in an organic solvent solution that forms a first water-in-oil (w/o) emulsion.

20. The formulation as in claim 11, wherein the concentration of tricaprylin is from about 5 to about 80 mM in an organic solvent solution that forms a first water-in-oil (w/o) emulsion.

21. The formulation as in claim 1, wherein the plasma $C_{max}$ of said methotrexate of from 5% to about 35% of the plasma $C_{max}$ of immediate release dosage forms of methotrexate.

22. The formulation as in claim 1, wherein the plasma $C_{max}$ of said methotrexate of from 5% to about 11% of the plasma $C_{max}$ of immediate release dosage forms of methotrexate.

23. The formulation as in claim 1, wherein the molar ratio of said one or more amphipathic lipids to said one or more neutral lipids is about 4 to 5.

24. The formulation as in claim 1, wherein the molar ratio of said one or more amphipathic lipids to said one or more neutral lipids is about 9 to 11.

* * * * *

UNITED STATES PATENT AND TRADEMARK OFFICE
CERTIFICATE OF CORRECTION

PATENT NO. : 10,028,911 B2
APPLICATION NO. : 13/786323
DATED : July 24, 2018
INVENTOR(S) : Louie Daniel Garcia et al.

Page 1 of 2

It is certified that error appears in the above-identified patent and that said Letters Patent is hereby corrected as shown below:

On the Title Page

Item (57), Abstract at Line 1, after "Disclosed" delete "is".

In the Specification

In Column 1 at Lines 16-17 (approx.), change "ANTIREHEUMATIC" to --ANTIRHEUMATIC--.

In Column 1 at Line 58, change "then" to --than--.

In Column 2 at Line 15, change "mgc/L-hr." to --mcg/L-hr.--.

In Column 3 at Line 8, change "ore" to --or--.

In Column 3 at Line 18, change "(dioleylphosphatidylcholine" to --(dioleoylphosphatidylcholine--.

In Column 4 at Line 32 (approx.), change "hydatidform" to --hydatidiform--.

In Column 4 at Line 45, change "ore" to --or--.

In Column 6 at Lines 7-8, change "permicious" to --pernicious--.

In Column 6 at Line 36, change "hydatidform" to --hydatidiform--.

In Column 6 at Line 47, change "menningeal" to --meningeal--.

In Column 7 at Line 14, change "$C^-_{max}$" to --$C_{max}$--.

In Column 8 at Line 10, change "form" to --from--.

Signed and Sealed this
Thirteenth Day of November, 2018

Andrei Iancu
*Director of the United States Patent and Trademark Office*

CERTIFICATE OF CORRECTION (continued)
U.S. Pat. No. 10,028,911 B2

In Column 8 at Line 13, change "phosphaitdyclholines," to --phosphatidylcholines,--.

In Column 8 at Line 31, change "trilinoelin," to --trilinolein,--.

In Column 11 at Line 23, change "then was" to --then--.

In Column 14 at Line 63, change "Pharmacopeal" to --Pharmacopoeia--.

In Column 15 at Line 1, change "(2 S)-" to --(2S)- --.